(12) United States Patent
Anderson et al.

(10) Patent No.: US 6,352,513 B1
(45) Date of Patent: Mar. 5, 2002

(54) PERSONAL CERVICAL CELL COLLECTOR

(75) Inventors: David M. Anderson, Hinsdale; Peter P. Gombrich, Chicago; Richard A. Domanik, Libertyville, all of IL (US)

(73) Assignee: Ampersand Medical Corporation, Chicago, IL (US)

( * ) Notice: Subject to any disclaimer, the term of this patent is extended or adjusted under 35 U.S.C. 154(b) by 0 days.

(21) Appl. No.: 09/603,625

(22) Filed: Jun. 26, 2000

Related U.S. Application Data

(60) Provisional application No. 60/210,218, filed on Jun. 8, 2000, and provisional application No. 60/141,242, filed on Jun. 25, 1999.

(51) Int. Cl.[7] ............................................... A61B 10/00
(52) U.S. Cl. ........................... 600/572; 600/569; 604/1
(58) Field of Search ................................. 600/562, 569, 600/570, 572; 604/1, 327, 328, 330

(56) References Cited

U.S. PATENT DOCUMENTS

| 3,592,186 A | 7/1971 | Oster ......................... 600/570 |
| 3,664,328 A | 5/1972 | Moyle, Jr. et al. .......... 600/569 |
| 3,776,219 A | 12/1973 | Brown ....................... 600/572 |

(List continued on next page.)

OTHER PUBLICATIONS

International Search Report.

*Primary Examiner*—John P. Lacyk
*Assistant Examiner*—Charles Marmor, II
(74) *Attorney, Agent, or Firm*—Merchant & Gould P.C.

(57) ABSTRACT

A cervical cell collection device can easily and comfortably be used by a woman in the privacy and comfort of her own home. Once the woman obtains the cervical cell sample, she can be forward it to a physician's office or other lab location for analysis. The collection device includes an outer guide assembly and an inner sampling assembly bearing a collector.

37 Claims, 12 Drawing Sheets

U.S. PATENT DOCUMENTS

| | | | |
|---|---|---|---|
| 3,995,618 A | 12/1976 | Kingsley et al. | 600/572 |
| 4,023,559 A * | 5/1977 | Gaskell | 600/572 |
| 4,131,112 A | 12/1978 | Kopito et al. | 600/578 |
| 4,157,709 A | 6/1979 | Schuster et al. | 600/572 |
| 4,227,537 A | 10/1980 | Suciu et al. | 600/569 |
| 4,232,673 A | 11/1980 | Bucalo | 600/582 |
| 4,235,244 A | 11/1980 | Abele et al. | 600/562 |
| 4,245,653 A | 1/1981 | Weaver | 600/563 |
| 4,318,414 A | 3/1982 | Schuster et al. | 600/572 |
| 4,448,205 A | 5/1984 | Stenkvist | 600/562 |
| 4,467,816 A | 8/1984 | Schluter | 600/569 |
| 4,485,824 A | 12/1984 | Koll | 600/569 |
| 5,370,128 A | 12/1984 | Wainwright | 600/569 |
| 4,586,604 A | 5/1986 | Alter | 206/210 |
| 4,628,941 A | 12/1986 | Kosasky | 600/572 |
| 4,633,886 A | 1/1987 | Bucaro et al. | 600/562 |
| 4,653,510 A | 3/1987 | Koll | 600/569 |
| 4,662,381 A | 5/1987 | Inaba | 600/569 |
| 4,700,713 A | 10/1987 | Kist | 600/569 |
| 4,754,764 A | 7/1988 | Bayne | 600/569 |
| 4,762,133 A | 8/1988 | Bayne et al. | 600/569 |
| 4,784,158 A | 11/1988 | Okimoto | 600/572 |
| 4,862,899 A | 9/1989 | Bucaro | 600/562 |
| 4,873,992 A | 10/1989 | Bayne | 600/569 |
| 4,877,037 A | 10/1989 | Ko et al. | 600/569 |
| 4,945,921 A | 8/1990 | Okimoto | 600/572 |
| 4,953,560 A | 9/1990 | Samuels | 600/572 |
| 5,022,408 A | 6/1991 | Mohajer | 600/569 |
| 5,121,752 A | 6/1992 | Canna | 600/572 |
| 5,129,402 A | 7/1992 | Koll et al. | 600/572 |
| 5,191,899 A | 3/1993 | Strickland et al. | 600/569 |
| 5,201,323 A | 4/1993 | Vermeulen | 600/569 |
| 5,253,652 A | 10/1993 | Fast | 600/569 |
| 5,259,391 A | 11/1993 | Altshuler et al. | 600/572 |
| 5,339,828 A | 8/1994 | Keating et al. | 600/572 |
| 5,397,312 A | 3/1995 | Rademaker et al. | 604/218 |
| 5,445,164 A | 8/1995 | Worthen et al. | 600/572 |
| 5,456,265 A | 10/1995 | Yim | 600/569 |
| 5,462,063 A | 10/1995 | Kist et al. | 600/569 |
| 5,522,795 A | 6/1996 | Green et al. | 604/1 |
| 5,535,756 A | 7/1996 | Parasher | 600/569 |
| 5,623,941 A | 4/1997 | Hedberg et al. | 600/569 |
| 5,738,109 A | 4/1998 | Parasher | 600/569 |
| 5,787,891 A | 8/1998 | Sak | 600/569 |
| 5,792,074 A | 8/1998 | Turkel et al. | 600/569 |
| 5,795,309 A | 8/1998 | Leet et al. | 600/569 |
| 6,036,658 A * | 3/2000 | Leet et al. | 600/569 |
| 6,059,735 A * | 5/2000 | Sgro | 600/569 |
| 6,155,990 A * | 12/2000 | Fournier | 600/572 |

* cited by examiner

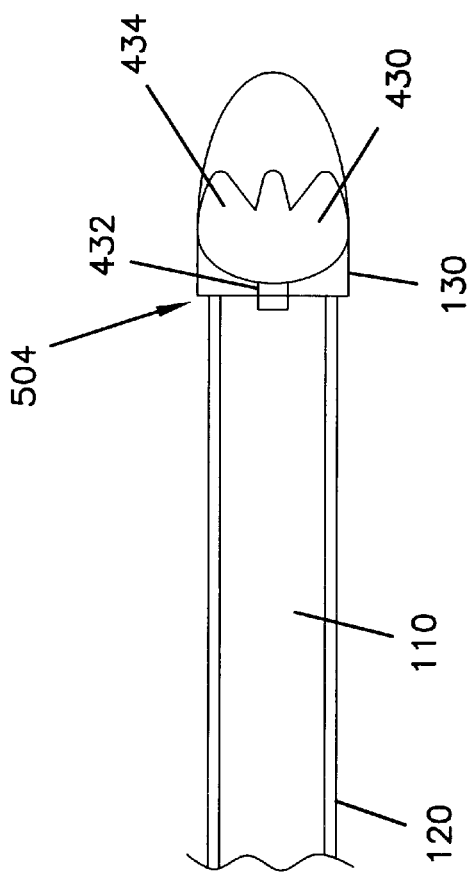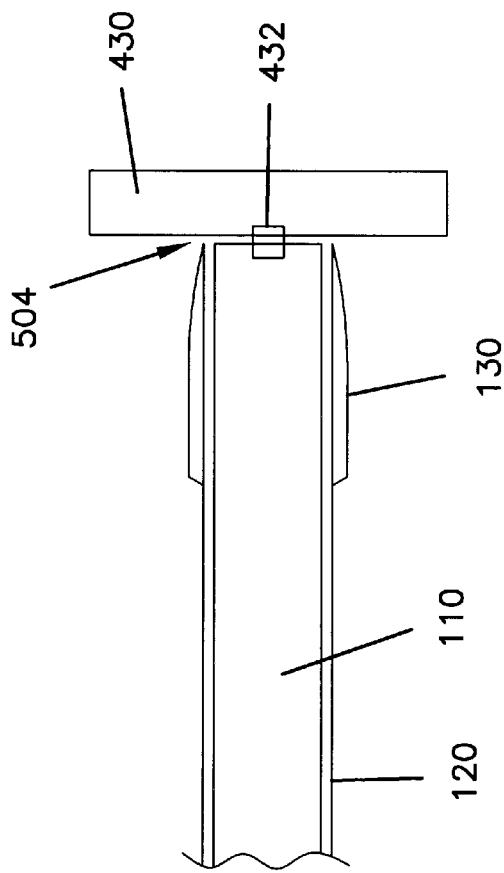
FIG. 4
FIG. 5

PERSONAL CERVICAL CELL COLLECTOR

RELATED APPLICATIONS

This application claims priority to provisional application Serial No. 60/141,242, filed Jun. 25, 1999 entitled "PERSONAL CERVICAL SAMPLE COLLECTION SYSTEM" and provisional application Serial No. 60/210,218, filed Jun. 8, 2000, entitled "PERSONAL CERVICAL CELL SPECIMEN COLLECTOR". Both applications are specifically incorporated by reference herein.

TECHNICAL FIELD

The invention relates generally to cervical cell sampling and more specifically to devices and methods whereby cervical cell samples can be personally collected by a patient. The invention relates to devices and methods in which the cervical cell samples are collected by the patient and then forwarded to a physician or lab for analysis.

BACKGROUND

Cervical cancer is a leading form of cancer among women. In the United States alone, there are believed to be more than two million cases of precancerous cervical abnormalities annually. The U.S. also sees, on average, about sixty five thousand cases of cervical carcinoma and about sixteen thousand cases of invasive cervical cancer. Although screening is less common outside the Unites States, nearly half a million cases of cervical cancer are detected each year around the world.

Cervical cancer frequently begins as a precancerous lesion of the cervix. These lesions are also known as cervical intraepithelial neoplasia. If left untreated, these lesions can deepen over time and ultimately develop into an invasive cancer of the cervix and associated tissues. Fortunately, early detection followed by appropriate treatment results in a very high cure rate for cervical cancer.

Therefore, it is quite important that at least certain factions of the female population undergo regular screening. These factions include patients with previous cervical abnormalities and those who have a family history of cervical abnormalities. Women who are sexually active are at greater risk and should undergo regular screening, as are those who test positive for HPV (human papillomavirus). This is a sexually transmitted virus that in some forms can cause genital warts.

During the 1940's, Dr. George Papanicolaou developed a screening test which bears his name and which has become the most widely used screening technique for detecting abnormal cervical cells. Today, this test is known more commonly as the PAP test or the PAP smear test. Typically, the PAP test is performed in the physician's office as part of a woman's routine gynecological examination. The test involves collecting cervical cells via a brush, stick or swab that is used to loosen and then collect cells that can be examined microscopically.

Typically, the PAP test is performed by inserting a speculum into the patient's vagina to expose the cervix. The surface of the cervix is then scraped by a brush, stick or swab and the exfoliated cells thereby collected are smeared upon a microscope slide for cytological examination. There are a number of drawbacks to the PAP test.

The PAP test is nearly always performed in a physician's office by a gynecologist or other medical professional. Thus, the test is not inexpensive, as the expense of an office visit is necessarily included. This means that the PAP test is not readily available to all women, for example, as would be desired in public health screening. Further, the test is considered by many women to be uncomfortable and embarrassing. Some women have religious beliefs that prohibit gynecological procedures such as the PAP test.

Although most medical professionals consider the PAP test something that should be done throughout the later stages of a woman's life, many women avoid the gynecologist once they are done bearing children. Thus, a need remains for an apparatus that will extend cervical screening to more women by permitting women to easily and comfortably obtain a cervical cell sample without requiring a physician's assistance. Such an apparatus could be used, for example, to augment traditional PAP tests by providing cervical cell screening to women who would otherwise not have a PAP test. A personal cervical cell collector could also be used to confirm a previous diagnosis.

SUMMARY OF THE INVENTION

Accordingly, the invention relates to a personal collector that can easily and comfortably be used by a woman in the privacy and comfort of her own home. Once the cervical sample is obtained, it can be forwarded to a physician's office or other lab location for analysis. If the subsequent analysis proves positive, the woman can then be seen by a physician.

The invention can be found in a cervical cell collection apparatus that is intended for personal use. The collection apparatus includes an outer guide assembly curved to approximate the natural curvature of a woman's vagina. An inner sampling assembly positioned within the outer guide assembly is also included. The inner sampling assembly includes a collector pad and is moveable from a first position in which the collector pad is located within the outer guide assembly to a second position in which the collector pad is located outside the outer guide assembly. The inner sampling assembly is configured to collect cervical cells while in the second position while the collector pad is protected against unwanted sample contamination while in the first position.

In another embodiment, the collection apparatus includes an outer guide assembly curved to approximate the natural curvature of a woman's vagina, wherein the outer guide assembly includes a protective tip. An inner sampling assembly positioned within the outer guide assembly is also included. The inner sampling assembly includes a flexible shaft bearing a collector pad at a first end and a gripping structure at a second end, and is moveable from a first position in which the collector pad is located within the outer guide assembly to a second position in which the collector pad is located outside the outer guide assembly. The inner sampling assembly is configured to collect cervical cells while in the second position while the collector pad is protected against unwanted sample contamination while in the first position.

The invention is also found in a personal cervical cell collection kit that includes a personal collector and a fixative canister. The personal collector is as described above, while the fixative canister includes an outer shell and an inner cap that fits within the outer shell but is configured to receive the protective tip of the personal collector. The fixative canister also includes a unit dose container that contains a volume of fixative and that has an easily piercable or frangible segment. An outer cap that is configured to cover an end of the outer shell is also included.

The invention is also found in a method of obtaining a cervical cell sample without requiring the assistance of medical personal. The method includes obtaining a kit having a personal collector and a fixative container, wherein the personal collector includes a sampling collector pad. The personal collector is inserted into the vagina until the personal collector contacts the cervix, at which point mucus is removed from the cervix. The sampling collector pad collects a cervical cell sample and is then withdrawn back into the personal collector, which is then withdrawn from the vagina. The sampling collector pad is inserted into the fixative container to preserve the cervical cell sample.

In another embodiment, the personal collector includes a protective tip that serves to remove mucus from the cervix prior to sampling, thereby yielding a cleaner sample that is less likely to contaminated.

Other features and advantages of the present invention will be apparent from the following detailed description and drawings.

BRIEF DESCRIPTION OF THE FIGURES

FIG. 4 is a partial cutaway view of the personal collector of FIG. 1, illustrating the packed or retracted position of a particular embodiment of the collector pad.

FIG. 5 is a partial cutaway view of the personal collector of FIG. 1, illustrating the extended position of the collector pad shown in FIG. 4.

DETAILED DESCRIPTION OF PRESENTLY PREFERRED EMBODIMENTS

The invention concerns a personal collector that a woman can use in the privacy of her own home to collect cervical cell samples in a simple and comfortable manner. Preferably, the cervical cell samples are collected in such a way as to minimize or even eliminate possible contamination of the sample with other materials typically present in the vaginal tract. Once collected, the cervical cell samples are preferably transferred into a device suitable to preserve the cells until the cells can be further processed and analyzed.

A typical manner of processing and analyzing cervical cell samples is to place the cells onto a microscope for morphological examination in which a technician examines the cells for visible signs of abnormality. If such are found, additional testing of the patient may be required. This general analysis is typical of the testing used to examine PAP smear samples, as is well known by those of skill in the art.

Figure 1:
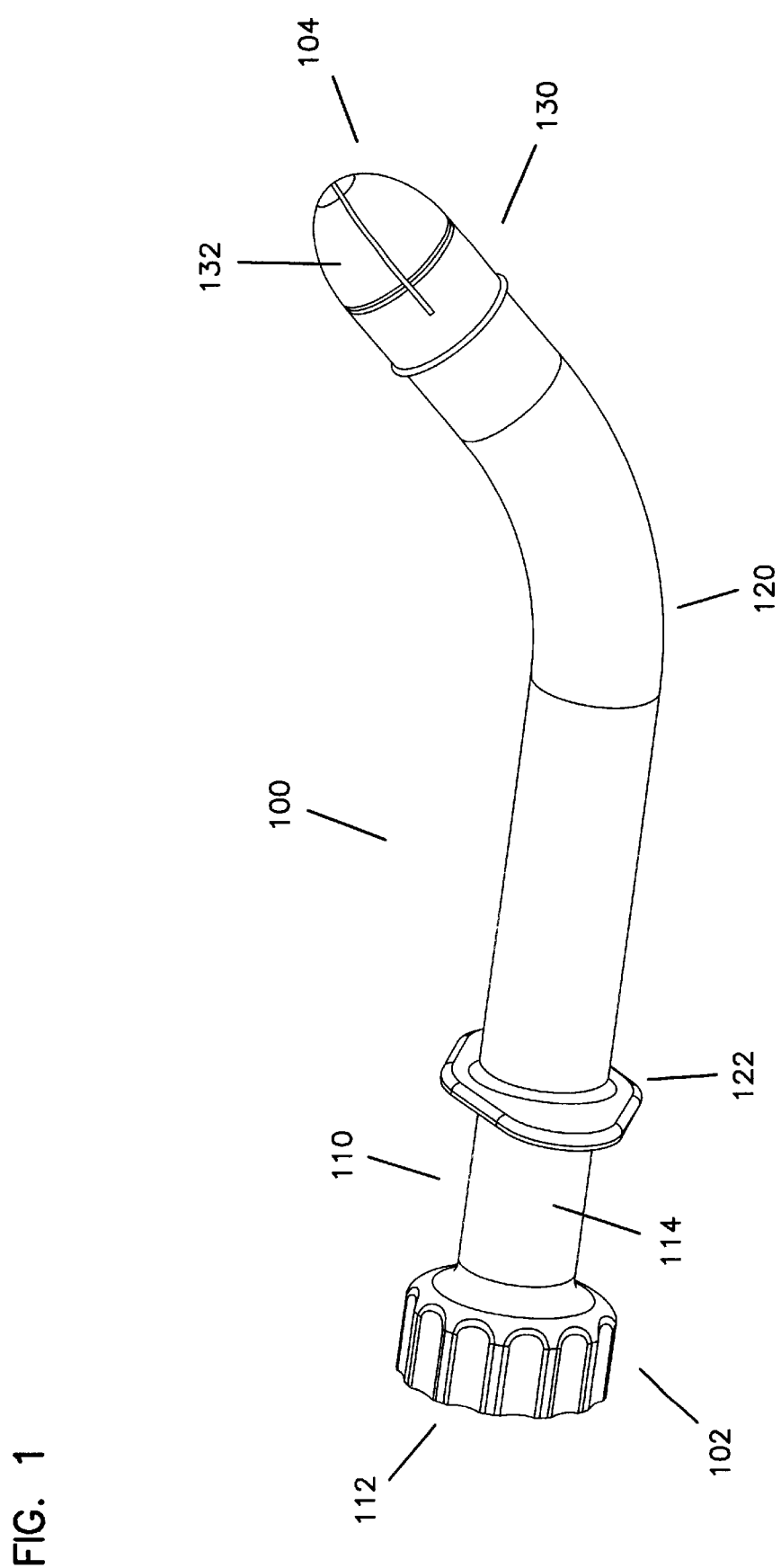
FIG. 1 is a perspective view of a personal collector in accordance with a preferred embodiment of the invention.

Referring now to the drawings, wherein similar reference numerals indicate similar elements in a number of drawings, there is shown in FIG. 1 a personal collector 100 in accordance with a preferred embodiment of the present invention. The personal collector 100 includes an outer guide assembly 120 and an inner sampling assembly 110. A handle 112 is located at the proximal end 102 of the inner sampling assembly 110. In this, and throughout this disclosure, a proximal position is considered to be closest to the end of the personal collector 100 that remains outside the body (the handle) while a distal position is considered to be the opposite end, or the portion of the personal collector 100 that enters the body.

Figure 2:
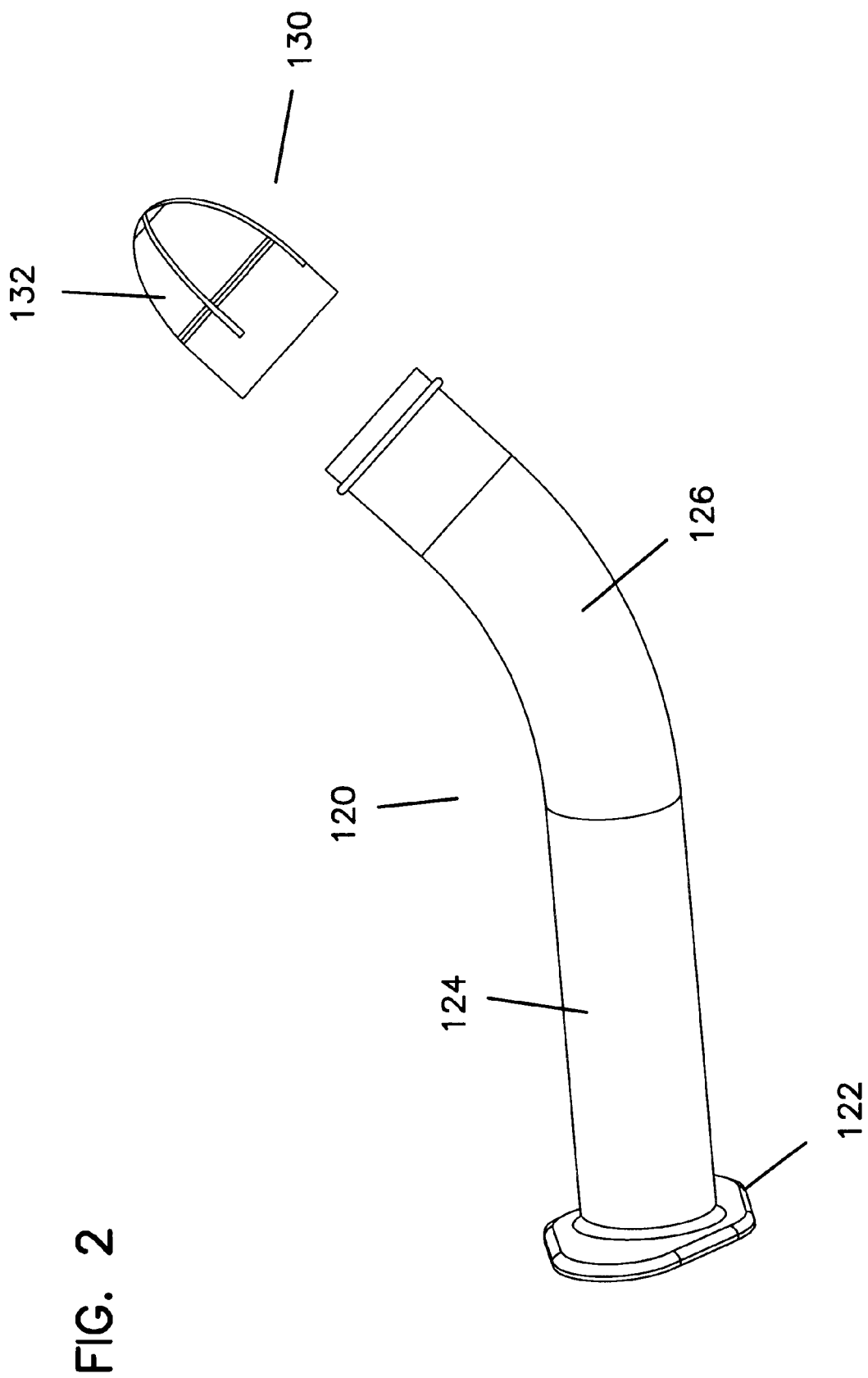
FIG. 2 is a perspective view of the outer guide assembly of the personal collector shown in FIG. 1.

Outer guide assembly 120 (see also FIG. 2) is a hollow, substantially circular cylinder that is preferably is curved to approximate the natural geometry of the vaginal tract when a woman is in a sitting or standing position, as these positions are more likely to be used by the woman in taking a cervical cell sample. While the outer guide assembly 120 can also be substantially linear, such a shape is more suited to the vaginal tract geometry obtained when the woman being examined is in the standard position for a gynecological examination, i.e. in the stirrups.

The outer guide assembly 120 can be gently curved over its entire length, but that can perhaps lead to difficulties in guiding the assembly into and through the vagina during use, as well as being able to rotate the personal collector 100 once it has been fuly inserted into the vagina. Therefore, it is preferable that the outer guide assembly 120 include a substantially linear portion 124 and a curved portion 126 as illustrated in, for example, FIG. 2. Preferably, the linear portion 124 has a length of from about 25 to about 75 millimeters while the curved portion preferably has a length of about 20 to about 60 millimeters. If the entire length of the outer guide assembly 120 is curved, it preferably has a radius of curvature of about 30 to 70 millimeters. If, however, only a portion is curved, that curved portion 126 preferably has a radius of curvature of about 40 to 60 millimeters.

As illustrated, the outer guide assembly 120 is substantially circular in cross-section. It has been found that a substantially circular cross-section provides for the most efficient use of the interior volume of the outer guide assembly 120. This shape also has manufacturing advantages. One of skill in the art will realize, however, that the outer guide assembly 120 can have other cross-sectional geometries and still function as intended.

The outer guide 120 also has a protective tip 130 located at the distal end 104 (as seen in FIG. 1) of the personal collector 100. The protective tip 130 provides several functions. It serves to protect the collector pad 430 as seen in FIG. 4 during both insertion into and withdrawal from (the personal collector 100) the user's vagina. Preferably, the protective tip 130 also serves to remove at least a portion of the mucus and other material typically found on and near the cervix. The protective tip 130 can be coated with or even be made from a substance that can function as desired. This can include cilia-like structures or fabric-like materials such as flocking.

Figure 6:
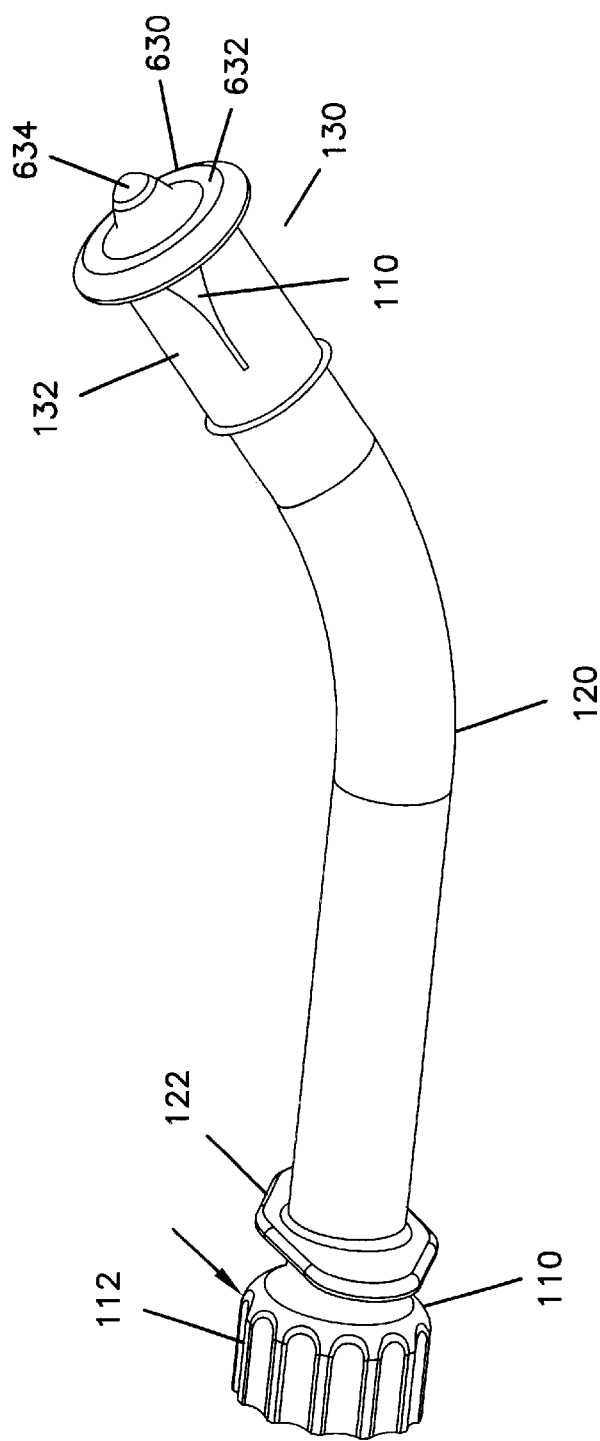
FIG. 6 is a perspective view of the personal collector of FIG. 1, illustrating an alternate embodiment of the collector pad in a partially extended position. This Figure also shows a preferred embodiment of the protective tip located at the distal end of the outer guide assembly.

FIG. 6 illustrates how a preferred embodiment of the protective tip 130 functions. Preferably, the protective tip 130 has a number of individual sections or petal-like structures 132 that can open as the inner sampling assembly 110 is moved towards an extended position in which the collector pad 630 has moved beyond the confines of the outer guide assembly 120 and is positioned for cervical cell sampling. Preferably, the individual sections 132 can return to their original positions (as in FIG. 1) once the inner sampling assembly 110 is retracted. In a preferred embodiment, the individual sections 132 are biased in a closed position.

The outer guide assembly 120 preferably includes a finger grip 122 which, as described in greater detail hereinafter, provides assistance in positioning and operating the personal collector 100. Similarly, inner sampling assembly 110 has a handle 112 that will also be described in greater detail.

Figure 3:
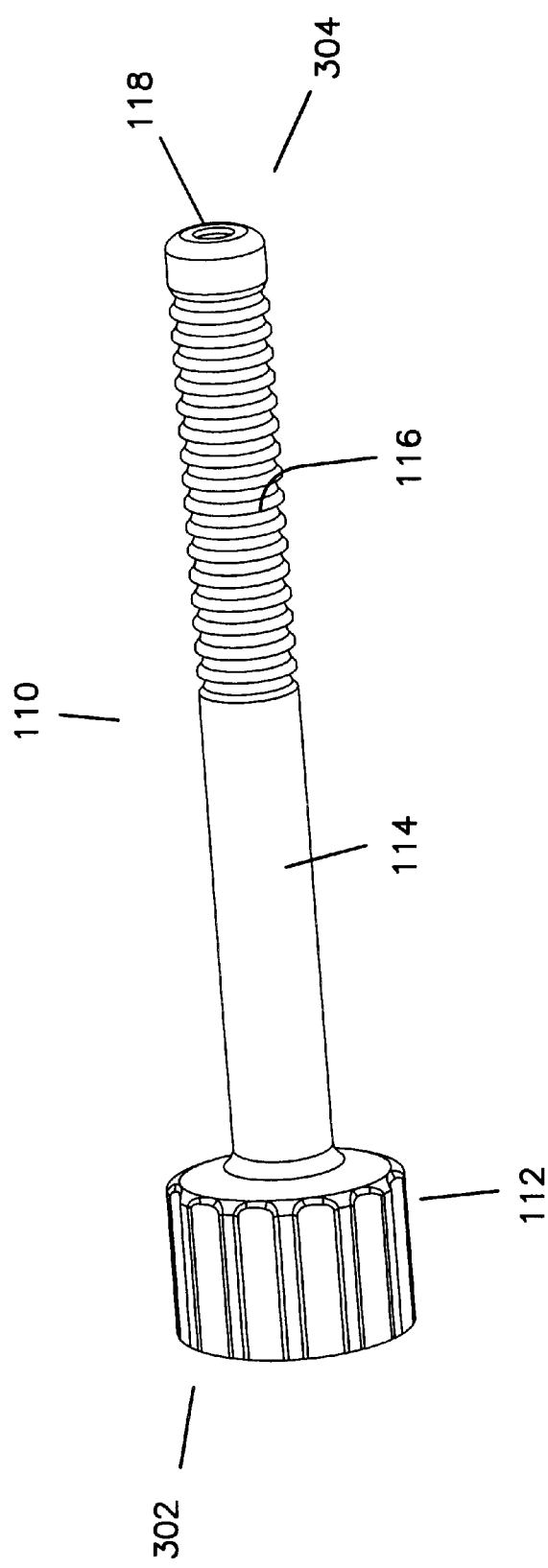
FIG. 3 is a perspective view of the inner sampling assembly of the personal collector shown in FIG. 1.

Inner sampling assembly 110 is perhaps best illustrated in FIG. 3. In a preferred embodiment, the inner sampling assembly 110 includes a smooth, substantially rigid cylindrical portion 114 and a flexible portion 116. The flexible portion 116 provides the inner sampling assembly 110 with the flexibility that is beneficial for allowing telescopic movement within the outer guide assembly 120 while the substantially smooth portion 114 provides the stiffness useful in forcing the inner sampling assembly 110 through the outer guide assembly 120.

Alternatively, the flexible portion 116 can extend the entire length of the inner sampling assembly 110, from the handle 112 located at the proximal end 302 to the collector mounting point 118 located at the distal end 304, or any fraction thereof. Adjustments made in the length of the flexible portion 116 relative to the smooth, relatively rigid portion 114 can provide a desired level of flexibility in the inner sampling assembly 110 independently of the particular material used to form the inner sampling assembly 110. One of skill in the art will realize that flexible portion 116 does not have to be ribbed (as illustrated), but rather can be made from a material having the desired flexibility.

Both the inner sampling assembly 110 and the outer guide assembly 120 can be made from a variety of different materials. Preferably, these materials are biocompatible, meaning that they neither negatively impact the internal tissues of the body nor are themselves effected by bodily tissues and fluids. A number of plastics qualify, including, for example, polyethylene, polyvinyl chloride (PVC) and polystyrene. One of skill in the polymer field can readily create a material having desired characteristics from a variety of different plastics, simply by fine tuning the processes used to create them. It is possible that either the inner sampling assembly 110, outer guide assembly 120 or both be made from cardboard or other paper stock products exhibiting desirable strength, flexibility and resistance to moisture.

The handle 112 is located at the proximal end 302 (as shown in FIG. 3) of the inner sampling assembly 110. Use of the handle 112 will be described hereinafter in greater detail, although it can be said that the handle aids in operation of the personal collector 100. A preferred embodiment of the handle 112 is seen in the Figures, in which the handle 112 is seen as an enlarged portion of the smooth portion 114 of the inner sampling assembly 110. The handle 112 can be formed as an integral part of the smooth portion 114 or it can be formed separately and then adhered to the inner sampling assembly 110. The handle 112 as shown is scalloped, although a variety of other shapes and textures are possible, as known to those of skill in the art. The handle 112, the rigid portion 114 and the flexible portion 116 are together considered to provide a grippable pusher that is used (as described hereinafter) to control the position of the collector pad 430.

A collector mounting position 118 is found at the distal end 304 of the inner sampling assembly 110 and serves as a location at which the collector pad 430 can be mounted. FIGS. 4 and 5 illustrate the retracted and extended positions, respectively, of a preferred collector pad 430 while FIG. 6 illustrates the extended position of an alternative collector pad 630. The collector pad 630 comprises a substantially disk-shaped portion 632 and a centrally located raised portion 634. Preferably, the disk-shaped portion 632 is sized and configured to sample primarily the outer or ecto-cervical region while the raised portion 634 is sized and configured to sample primarily the inner or endo-cervical region. Preferably, both portions 632, 634 are able to sample the transition zone that lies between the inner and outer portions of the cervix. While not explicitly illustrated, the disk-shaped portion 632 and centrally located raised portion 634 can include, respectively, a large foam disk as portion 632 and a smaller foam disk as portion 634.

While several specific collector pad shapes are illustrated, the collector pad can have a variety of different geometric configurations. The limiting factor is whether or not the collector pad presents a sufficient surface area to the cervix for exfoliating and collecting cervical cells. For example, a cone-shaped collector pad could be used, with the large end of the cone presented towards the cervix if primarily ecto-cervical sampling is desired. Alternatively, the small end of the cone can be presented towards the cervix to enable primarily endo-cervical sampling.

The collector pad 430 can be made from a variety of materials, although foam has been found to be most useful. The foam can be open-celled or closed-cell, although open-celled foam is preferred. Other suitable materials include cloth and open-celled porous materials such as sponge. The collector pad 430 may be uncoated, or at least part of the collector can be coated with a substance such as collagen that enhances either the cell exfoliation or cell adherence characteristics of the collector. The collector pad 430 can also be coated with an adhesive. Alternatively, it is envisioned that at least part of the collector could instead be coated with a substance that would instead inhibit adherence by non-cervical cell materials.

The collector pad 430 is attached to the distal end 504 of the inner sampling assembly 110 through a snap-fit or other suitable connection. This is seen in FIGS. 4 and 5 as connection 432, which operably connects the collector pad 430 to the collector mounting position 118 (see FIG. 3). This connection could also be made with adhesives, although it is preferable in at least one embodiment of the invention that the collector pad be detachable once a cervical cell sample has been obtained. In a particular embodiment of the invention, an extraction string 1126 is attached to the collector pad 1130 (see FIG. 11, for example).

The inner sampling assembly 110 is configured to be moveable within the outer guide assembly 120. As such, the collector pad 430 is positioned within the outer guide assembly 120 both before use and after a sample is taken.

FIG. 4 illustrates how a preferred collector pad 430 is positioned within the protective tip 130. Preferably, the collector pad 430 is folded in such a way as to position the collector pad 430 in front of the inner sampling assembly 110. This can be seen in FIG. 4, where the collector pad 430 is folded into individual folds 434, each of which are located beyond the inner sampling assembly. In fact, the connection 432 is positioned between the distal end of the inner sampling assembly 110 and the collector pad 430.

Figure 9:
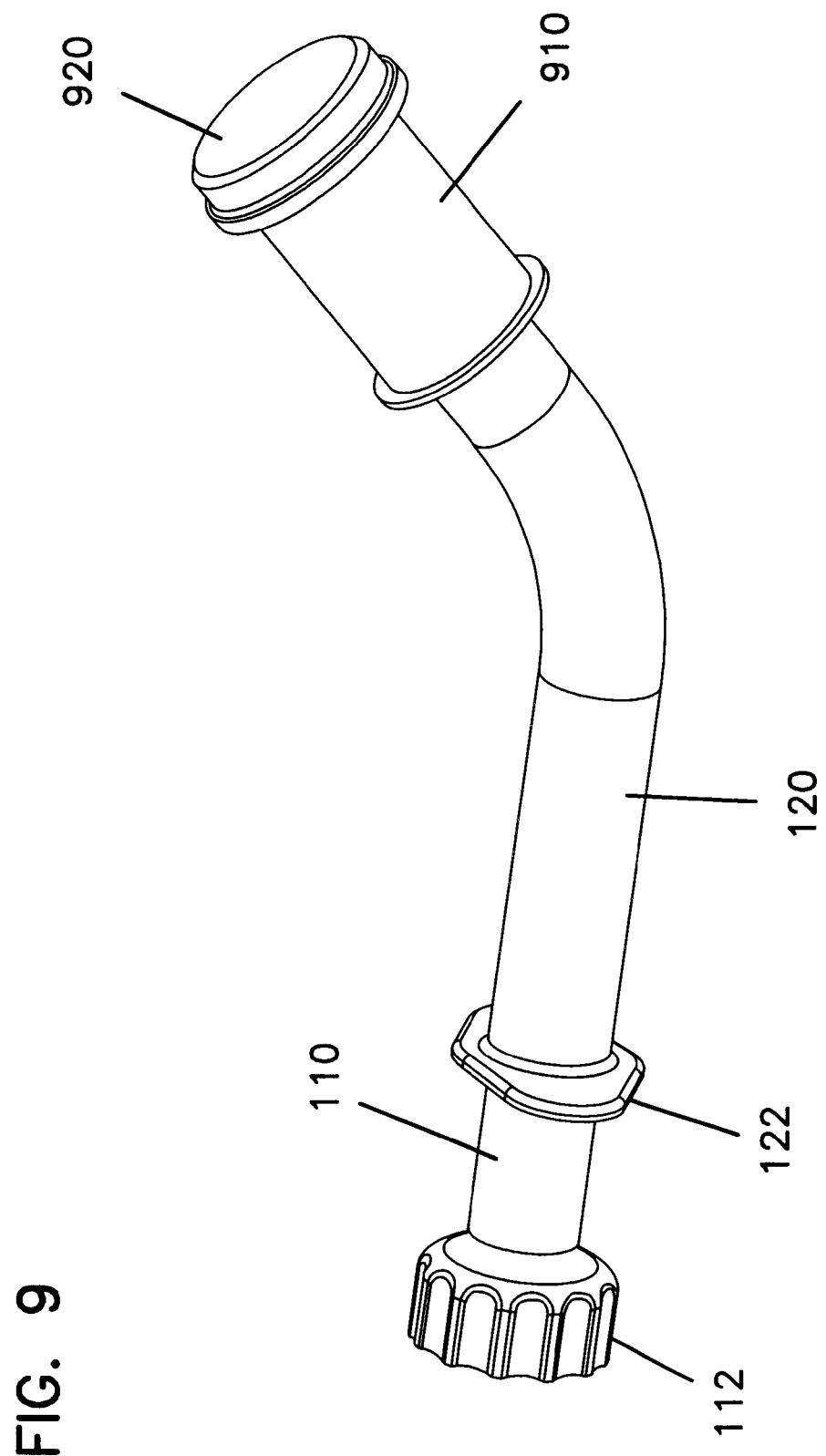
FIG. 9 is a perspective view of the personal collector of FIG. 1, shown in conjunction with a preferred sample retention system.

Operation of the personal collector 100 is as follows. Preferably, the user will obtain the personal collector 100 still attached to the fixative and protective canister 1000 as illustrated in FIG. 9.

Figure 7:
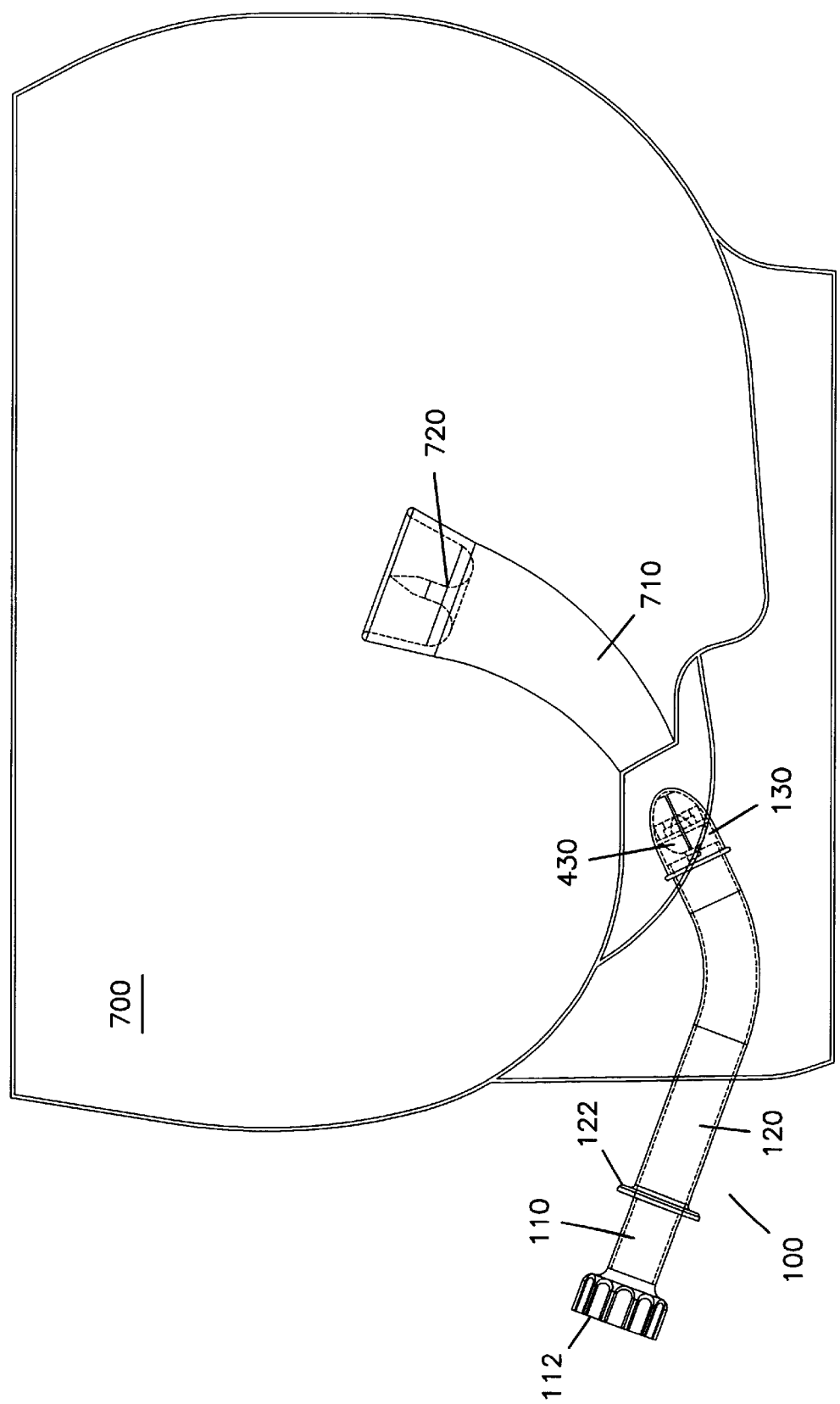
FIG. 7 is a schematic view illustrating placement of the personal collector of FIG. 1 just prior to insertion by the user.
Figure 8:
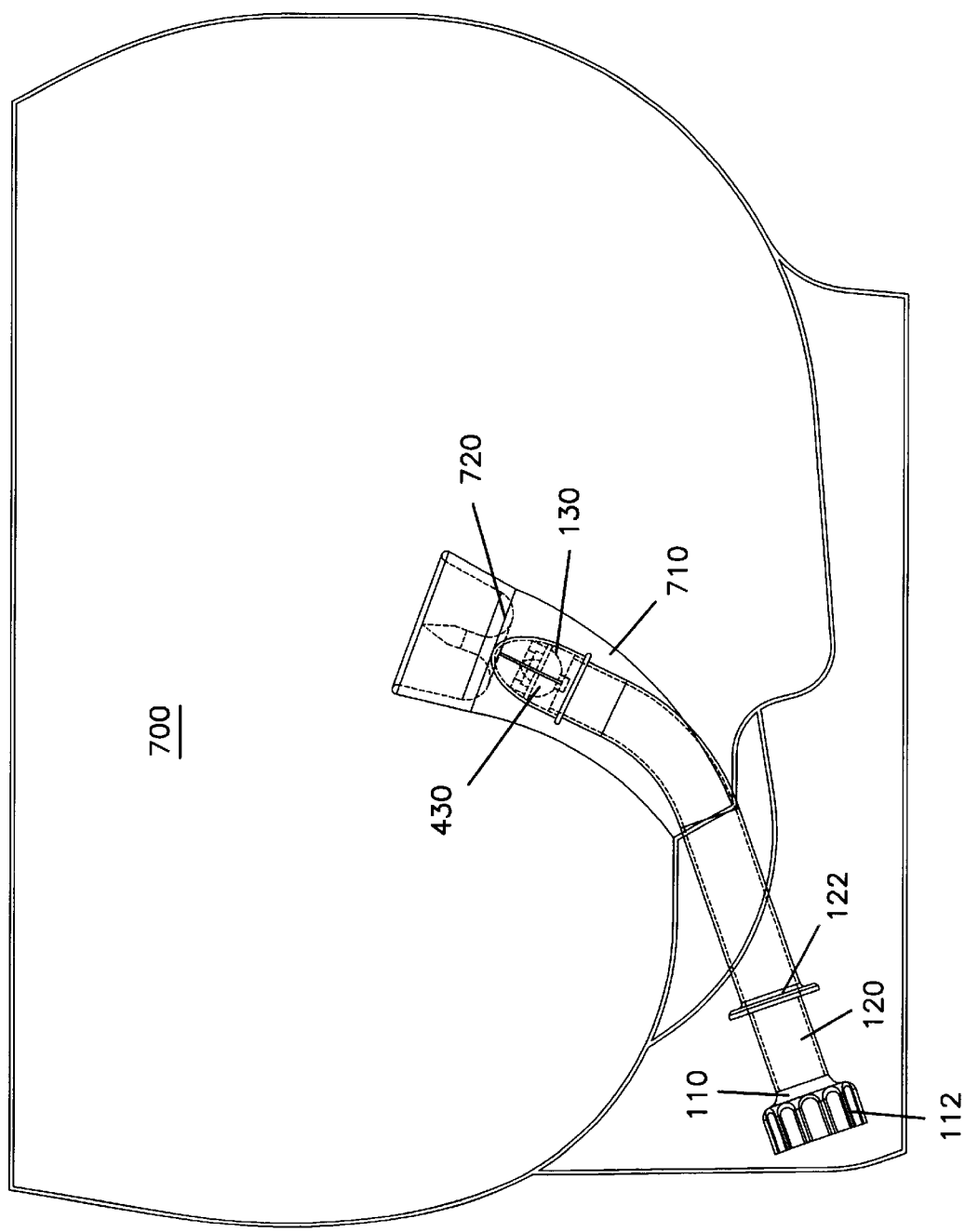
FIG. 8 is a schematic view illustrating placement of the personal collector of FIG. 1 fully positioned within the vagina of the user, with the protective tip positioned to remove mucus from the cervix.

In FIG. 7, the personal collector 100 is arranged for insertion. The inner sampling assembly 110 is in a retracted position with respect to the outer guide assembly 120. At this point, the personal collector 100 is positioned just outside the vagina 710. The relative position of the cervix 720 is seen as well in this rendition of the female anatomy 700. The personal collector 100 is then fully inserted into the vagina 710. Because the patient is unable to determine the position of the personal collector 100 in relation to her cervix 720, it is preferable that the patient simply insert the personal collector 100 as far as possible. Insertion is preferably limited by the protective tip 130 contacting the cervix 720, as illustrated in FIG. 8. This Figure also illustrates how the preferred curvature of the outer guide assembly 120 assists in negotiating the vaginal tract. Next, the user rotates the outer guide assembly 120 by grasping the finger holds 122 that are provided for that purpose. This is done so that the protective tip 130 can remove at least some of the mucus and other material typically found on and near the cervix 720

Next, the personal collector 100 is withdrawn slightly and the handle 112 is pushed until the collector pad 430 emerges from the outer guide assembly 120 and makes contact with the cervix 720. FIG. 6 illustrates how the protective tip 130 opens to permit the collector pad 430 to emerge.

With the collector pad 430 in full contact with the cervix 720, the user rotates the inner sampling assembly (and thus the collector pad 430) via handle 112. Then, the collector pad 430 is retracted back into the protective tip 130 by pulling back on the handle 112. At this point, the personal collector 100 can be removed from the vagina 710. The collector pad 430 is inserted into the fixative canister 1000 and preferably snaps into place. The remainder of the inner sampling assembly 110 and outer guide assembly 120 can be discarded. The cap 920 is then placed over the outer shell 910 of fixative canister 1000, which can then be sent for testing.

Figure 10:
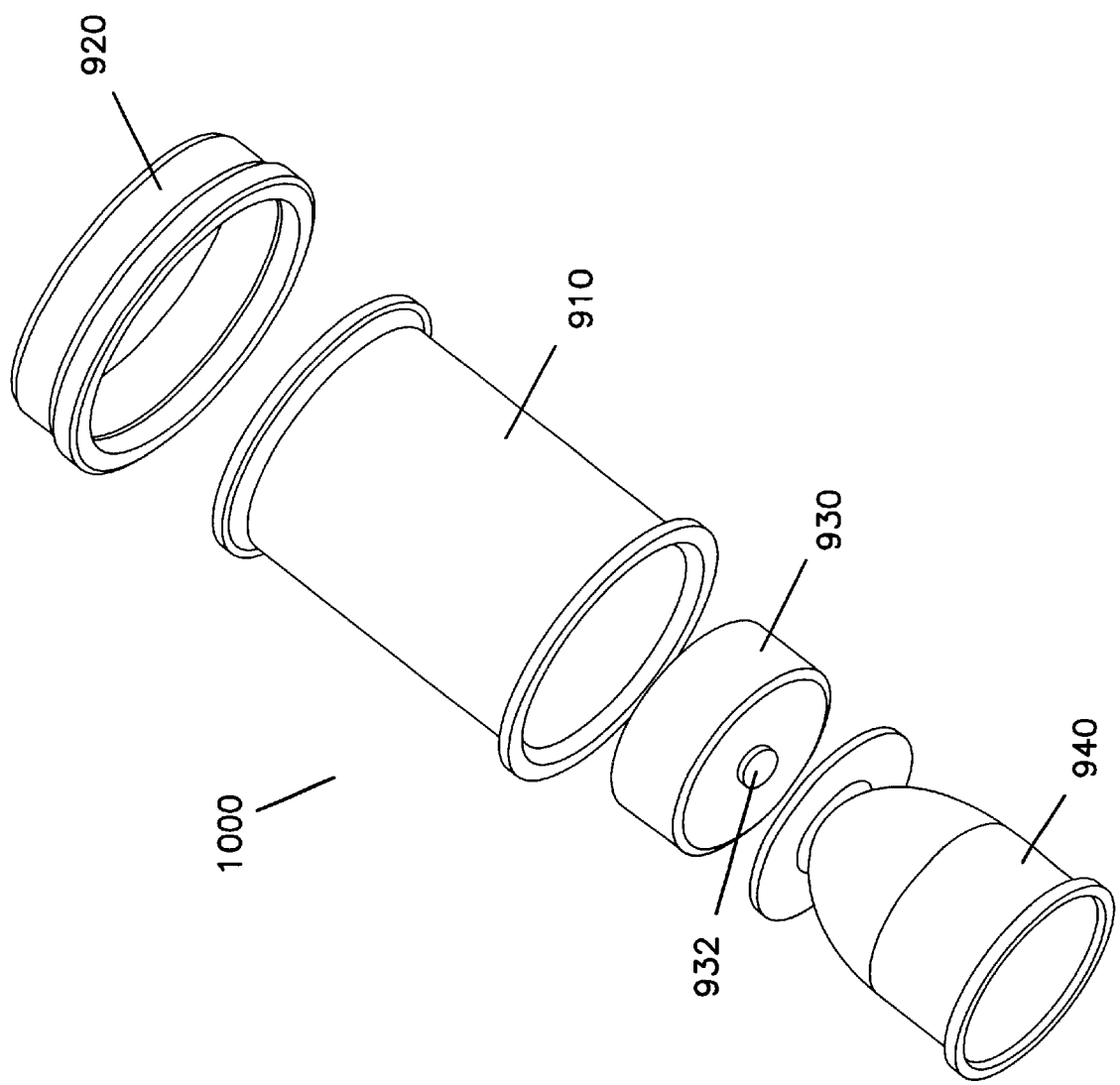
FIG. 10 is an exploded perspective view of the sample retention system shown in FIG. 9.

The fixative canister 1000, which is best described in reference to FIG. 10, serves to protect the protective tip 130 during shipping and handling. The fixative canister is removed prior to use of the personal collector 100, as referenced previously.

The fixative canister 1000 includes an outer shell 910, an inner cap 940 and a fixative dose container 930. The fixative dose container 930 includes a liquid fixative and has a pierceable seal 932 that will be punctured when the collector pad 430 is inserted. The fixative preferably includes mucolytic agents and red blood cell lysing agents, among others.

After sampling is complete, the collector pad 430 is reinserted into the fixative assembly 1000 so that the protective tip 130 is once again positioned within the inner cap 940. The collector pad 430 is then pushed firmly into the canister assembly 1000, thereby puncturing the fixative dose container 930 and allowing fixative to flow into the inner cap 940 and over the collector pad 430. Preferably, the inner sampling assembly 110 and the outer guide assembly 120 can be snapped off and discarded at this point. Finally, the cap 920 is placed over outer shell 910 to protect the sample.

An alternative embodiment of the invention involves a device that provides for the cell collector to remain in contact with the cervix for an extended period of time. There are a number of reasons why a physician may decide that extended sampling time is desirable, such as a low cell exfoliation rate, or if there is a low volume of cells within the exfoliated material.

The cell collector is preferably made from a thin-walled sponge material that is designed to accommodate an extraction string that is attached to an internal portion of the collector. The external part of the collector and its attached string are connected to a ring that is left in place as long as the collector is being worn within the vagina.

Preferably, the collector is inserted through a biodegradable hollow tube. The collector and tube can be provided as a ready for insertion package, with the tube and collector sealed within a disposable sterile bag or pouch. Once the collector has been inserted, the tube can be removed and disposed of, thereby leaving the collector in vivo for a given period of time. The collector can remain in vivo, in contact with the cervix, for as long as necessary to obtain a suitable sample. Preferably, this period of time is about 30 minutes.

Once the collector has been in contact with the cervix for a desired period of time, it is removed by pulling the ring through the tube, thereby turning the collector inside-out to protect the sample. The string is preferably attached to the non-expanded tube, so when the tube (ring) is pulled the collector (with the cervical sample contained therein) is pulled into the tube which is preferably sealed at the external (end opposite the vagina) end. Once the tube has been fully extended and the collector is inside the expanded tube, a cap or other closure is placed on the other (vaginal) end of the tube. When the cap or other closure is secured, a seal is broken in the cap or closure that releases an encapsulated preservative solution.

In an alternative embodiment, the collector can be fashioned with a ring structure along its outer diameter. In this case, the collector can be flattened and inserted into the vagina and placed in contact with the cervix much like a contraceptive diaphragm. The collector is preferably worn for a particular period of time, during which normal body motion will cause the collector to exfoliate cells from the cervix. Once the sampling period has ended, the user can remove the collector via an attached string or extended tab that can simply be grasped and pulled.

Preferably, the attached string or extended tab is attached at the center of the collector. If so, removal of the collector by pulling on the string or tab will essentially turn the collector inside-out. This protects the cervical cell sample from contamination by contacting the vaginal walls.

The sealed tube can be labeled and mailed in to a physician or other healthcare provider. In a preferred embodiment, it is envisioned that the sealed tube can be mailed directly to a lab for analysis, bypassing the physician. The personal collector described in this embodiment is intended to sample only the exocervical area. Thereby, the collector preferably forms (when released) a flexible cup that is about 30 to 35 millimeters in diameter and about 4–6 millimeters thick. Preferably, the sampling surface is mildly abrasive to assist in exfoliating cervical cells for sampling.

In a preferred embodiment, the collector is a thick, relatively flat elastomeric washer. The collector can have several laminate layers or can be a single material such as a foam. If a laminate is used, an inner layer can be a water impermeable polymer while the outer layer can be a sponge.

Figure 11:
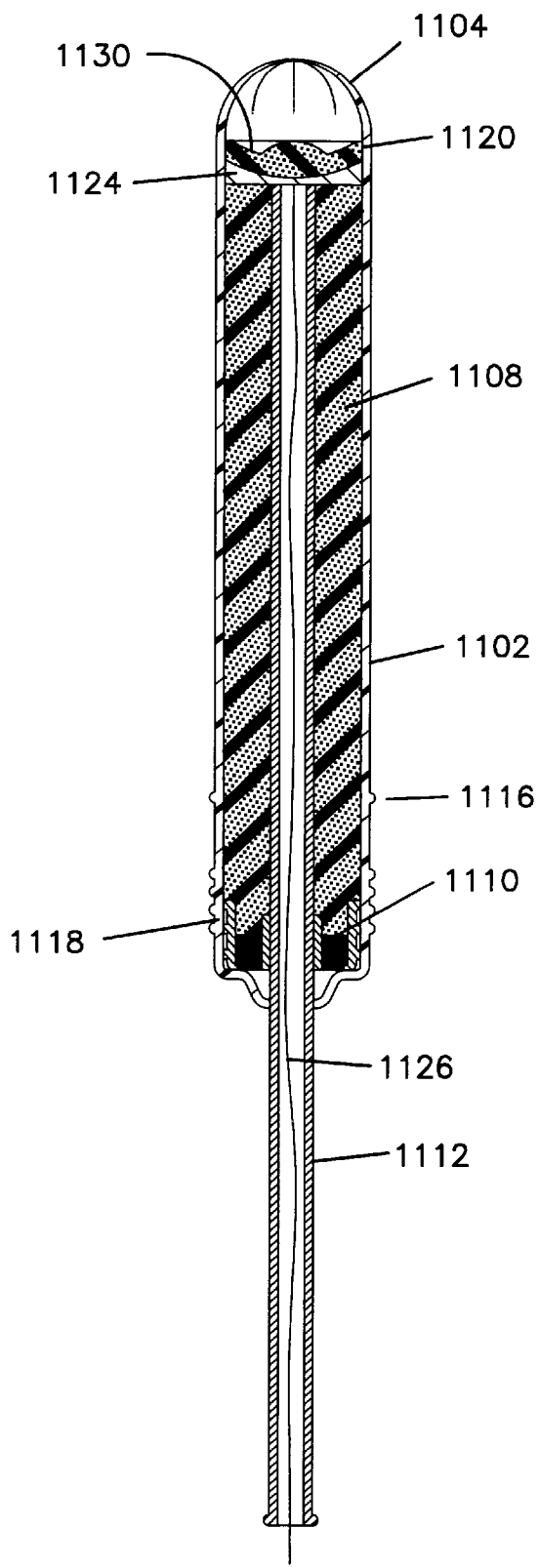
FIG. 11 is a sectional view of a personal collector according to an alternate embodiment of the invention.
Figure 12:
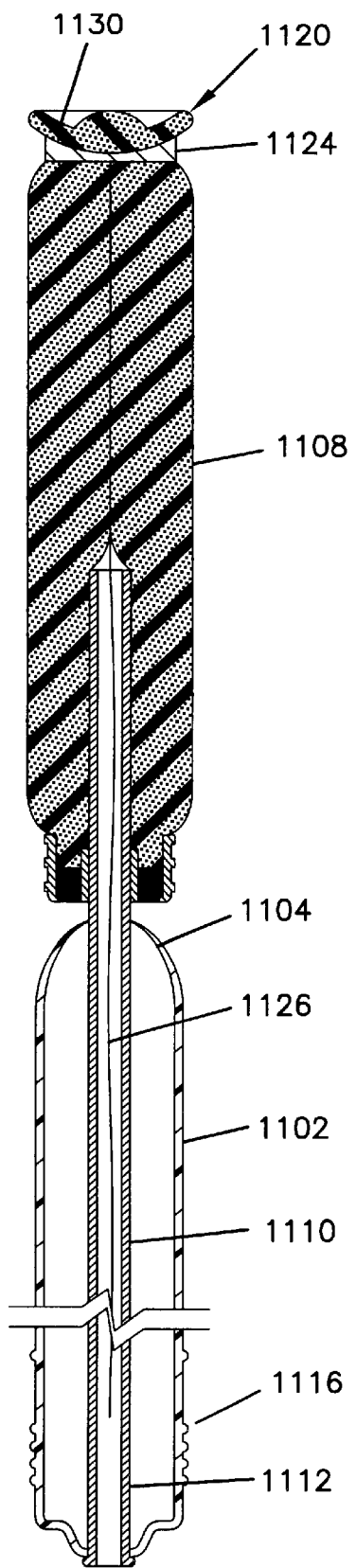
FIG. 12 is a sectional view of the personal collector of FIG. 11, showing the personal collector as configured while in the process of being inserted into a vagina.
Figure 13:
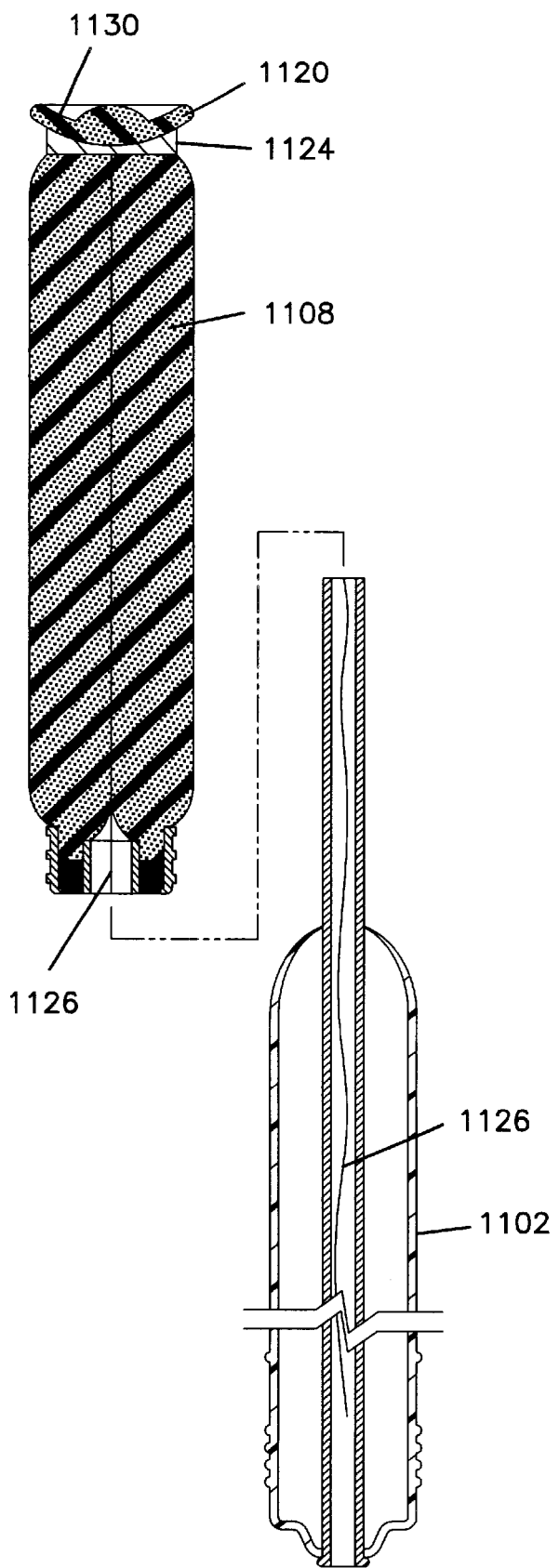
FIG. 13 is a sectional view of the personal collector of FIG. 11, showing the personal collector as temporarily worn within the vagina, with the insertion devices having been removed and discarded.

Returning to the Figures, the alternative embodiment described herein is illustrated in FIGS. 11–13. A guide tube 1102 that has distal petal elements 1104 compresses and surrounds the compressed foam cylinder 1108, which will function to hold the device within a user's vagina. An insert tube 1110 is located within the compressed foam cylinder 1118 and extends to provide a handle portion 1112. On the exterior of the tube 1102, an insertion location indicia ring 1116 provides guidance for proper device insertion and location. Although not required, it is preferable that the device include embossments 1118, which provide a grip area. At the distal end 1120, a collector sponge 1130 is mounted onto a preferably rigid disk 124. Preferably, the disk 1124 is engaged by the insert tube 1110 but is not permanently attached to the disk 1124. A withdrawal string 1126 extends from the disk 1124 down through the guide tube 1110.

In use, the assembled unit shown in FIG. 11 is inserted by the user into her vagina. The unit is inserted up to a depth equivalent to the location of the insertion indicia ring 1116. Then, while holding the insert tube 1112 in place with one hand, the user can gently remove the guide tube 1102 to leave the now un-compressed, radially expanded foam cylinder 1108 in place. Preferably, the foam cylinder 1108 is sized such that once expanded, it is firmly held in place by the vaginal walls (not seen in the Figures), as suggested in FIG. 12. Over a period of time, exfoliated cervical cells are collected on the sponge 1130.

As suggested in FIG. 13, the proximal end of the foam cylinder 1108 terminates in an open-ended ring or cap 1140 within which is a flexible membrane sack. When the user is ready to withdraw the sponge 1130 from her vagina, she holds the cap 1140 with one hand and draws down on the withdrawal string 1126 with her other hand. This slightly re-compresses the foam cylinder 1108 both radially and axially so as to pull the foam 1108 and collector disk 1124 into the membrane sack. This secures and protects the cervical cell sample.

The collector pad 430, 1130 can also be used to apply medications directly to the cervix. An example of a suitable drug is 8-amino levulinic acid, also known as ALA. This is a photodynamic therapy agent. One of skill will realize that a variety of other medications can also be applied in this manner.

While the invention has been described with reference to specific embodiments, it will be apparent to those skilled in the art that many alternatives, modifications and variations may be made. Accordingly, the present invention is intended to embrace all such alternatives, modifications and variations that may fall within the spirit and scope of the appended claims.

We claim:

1. A cervical cell collection apparatus intended for personal use, the collection apparatus comprising:
    an outer guide assembly curved to approximate the natural curvature of a woman's vagina, the outer guide assembly comprising a protective tip comprising an absorbent material;
    an inner sampling assembly positioned within the outer guide assembly, the inner sampling assembly comprising a collector pad, the inner sampling assembly moveable from a first position in which the collector pad is located within the outer guide assembly to a second position in which the collector pad is located outside the outer guide assembly;
    wherein the inner sampling assembly is configured to collect cervical cells while in the second position while the collector pad is protected against unwanted sample contamination while in the first position.

2. The collection apparatus of claim 1, wherein the absorbent material is adapted to remove mucus from the cervix.

3. The collection apparatus of claim 1, wherein the absorbent material comprises flocking.

4. The collection apparatus of claim 1, wherein the inner sampling assembly comprises a grippable pusher bearing the collector pad at one end thereof.

5. The collection apparatus of claim 1, wherein the collector pad comprises a material selected from the group consisting of cloth, sponge, foam and other open-celled porous materials.

6. The collection apparatus of claim 5, wherein the collector pad comprises a foam disk that has a diameter of about 25 millimeters and a thickness of about 6 millimeters.

7. The collection apparatus of claim 1, wherein the collector pad comprises two foam disks.

8. The collection apparatus of claim 7, wherein the collector pad comprises a large foam disk sized to sample an ecto-cervical region and a small foam disk sized to sample an endo-cervical region.

9. The collection apparatus of claim 1, wherein the outer guide assembly has a diameter that is less than about 13 millimeters.

10. The collection apparatus of claim 1, wherein the protective tip can reversibly open to allow passage of the inner sampling assembly.

11. The collection apparatus of claim 10, wherein the protective tip can close once the inner sampling assembly is withdrawn.

12. A cervical cell collection apparatus intended for personal use, the collection apparatus comprising:
    an outer guide assembly curved to approximate the natural curvature of a woman's vagina, the outer guide assembly comprising a mucus collector;
    an inner sampling assembly positioned within the outer guide assembly, the inner sampling assembly comprising a flexible shaft bearing a collector at a first end and a gripping structure at a second end, the inner sampling assembly moveable from a first position in which the collector is located within the outer guide assembly to a second position in which the collector is located outside the outer guide assembly;
    wherein the inner sampling assembly is configured to collect cervical cells while in the second position while the collector is protected against unwanted sample contamination while in the first position.

13. The collection apparatus of claim 12, wherein the collector comprises a material selected from the group consisting of cloth, sponge, foam and other open-celled porous materials.

14. The collection apparatus of claim 13, wherein the collector comprises a foam disk that has a diameter of about 25 millimeters and a thickness of about 6 millimeters.

15. The collection apparatus of claim 12, wherein the collector comprises two foam disks.

16. The collection apparatus of claim 15, wherein the collector comprises a large foam disk sized to sample an ecto-cervical region and a small foam disk sized to sample an endo-cervical region.

17. The collection apparatus of claim 12, wherein the outer guide assembly has a diameter that is less than about 13 millimeters.

18. The collection apparatus of claim 12, wherein the mucus collector can reversibly open to allow passage of the inner sampling assembly.

19. The collection apparatus of claim 18, wherein the mucus collector can close once the inner sampling assembly is withdrawn.

20. The collection apparatus of claim 12, wherein the mucus collector comprises an absorbent material.

21. The collection apparatus of claim 20, wherein the absorbent material comprises flocking.

22. A personal cervical cell collection kit, the kit comprising:
  a personal collector comprising:
    an outer guide assembly curved to approximate the natural curvature of a woman's vagina, the outer guide assembly comprising a protective tip comprising an absorbent material;
    an inner sampling assembly positioned within the outer guide assembly, the inner sampling assembly comprising a flexible shaft bearing a collector pad at a first end and a gripping structure at a second end, the inner sampling assembly moveable from a first position in which the collector pad is located within the outer guide assembly to a second position in which the collector pad is located outside the outer guide assembly;
    where in the inner sampling assembly is configured to collect cervical cell s while in the second position while the collector pad is protected against unwanted sample contamination while in the first position; and
  a fixative canister comprising:
    an outer shell;
    an inner cap that fits within the outer shell but is configured to receive the collector pad of the personal collector;
    a unit dose container comprising an easily pierceable segment, the dose container containing a volume of fixative; and
    an outer cap configured to cover an end of the outer shell.

23. The collection kit of claim 22, wherein the collector pad can puncture the easily pierceable segment of the unit dose container, thereby permitting the fixative to flow over the collector pad contained within the protective tip.

24. The collection kit of claim 22, wherein the collector pad comprises a material selected from the group consisting of cloth, sponge, foam and other open-celled porous materials.

25. The collection kit of claim 24, wherein the collector pad comprises a foam disk that has a diameter of about 25 millimeters and a thickness of about 6 millimeters.

26. The collection kit of claim 22, wherein the outer guide assembly has a diameter that is less than about 13 millimeters.

27. The collection kit of claim 22, wherein the protective tip can reversibly open to allow passage of the inner sampling assembly.

28. The collection kit of claim 27, wherein the protective tip can close once the inner sampling assembly is withdrawn.

29. The collection kit of claim 22, wherein the protective tip is configured such that it can remove at least some of any mucus found on the cervix.

30. The collection kit of claim 22, wherein the absorbent material comprises flocking.

31. A method of obtaining a cervical cell sample without requiring the assistance of medical personnel, the method comprising steps of:
  obtaining a kit comprising a personal collector and a fixative container, the personal collector comprising a sampling collector;
  inserting the personal collector into the vagina until the personal collector contacts the cervix;
  removing mucus from the cervix;
  partially withdrawing the personal collector;
  extending the sampling collector to contact the cervix;
  collecting a cervical cell sample;
  withdrawing the sampling collector back into the personal collector;
  withdrawing the personal collector from the vagina; and
  inserting the sampling collector into the fixative container to preserve the cervical cell sample.

32. The method of claim 31, wherein the step of removing mucus from the cervix comprises rotating the personal collector to remove the mucus.

33. The method of claim 31, wherein the step of collecting a cervical cell sample comprises rotating the personal collector.

34. The method of claim 31, wherein the step of collecting a cervical cell sample comprises leaving the sampling collector on contact with the cervix for an extended period of time.

35. The method of claim 34, wherein the step of withdrawing the sampling collector comprises using an extraction string to remove the sampling collector.

36. The method of claim 31, wherein the personal collector can be used to administer a medication directly to the cervix.

37. A personal cervical cell collection kit, the kit comprising:
  a personal collector comprising:
    an outer guide assembly curved to approximate the natural curvature of a woman's vagina, the outer guide assembly comprising a mucus collector;
    an inner sampling assembly positioned within the outer guide assembly, the inner sampling assembly comprising a flexible shaft bearing a collector pad at a first end and a gripping structure at a second end, the inner sampling assembly moveable from a first position in which the collector pad is located within the outer guide assembly to a second position in which the collector pad is located outside the outer guide assembly;
    wherein the inner sampling assembly is configured to collect cervical cells while in the second position while the collector pad is protected against unwanted sample contamination while in the first position; and
  a fixative canister comprising:
    an outer shell;
    an inner cap that fits within the outer shell but is configured to receive the collector pad of the personal collector;
    a unit dose container comprising an easily pierceable segment, the dose container containing a volume of fixative; and
    an outer cap configured to cover an end of the outer shell.

* * * * *